(12) United States Patent
Berthier et al.

(10) Patent No.: US 9,358,189 B2
(45) Date of Patent: Jun. 7, 2016

(54) STABLE FORMALDEHYDE-FREE MICROCAPSULES

(71) Applicants: Damien Berthier, Geneva (CH); Géraldine Leon, Geneva (CH); Nicolas Paret, Geneva (CH); Lahoussine Ouali, Geneva (CH)

(72) Inventors: Damien Berthier, Geneva (CH); Géraldine Leon, Geneva (CH); Nicolas Paret, Geneva (CH); Lahoussine Ouali, Geneva (CH)

(73) Assignee: Firmenich SA, Geneva (CH)

( * ) Notice: Subject to any disclaimer, the term of this patent is extended or adjusted under 35 U.S.C. 154(b) by 111 days.

(21) Appl. No.: 14/357,433

(22) PCT Filed: Oct. 29, 2012

(86) PCT No.: PCT/EP2012/071340
§ 371 (c)(1),
(2) Date: May 9, 2014

(87) PCT Pub. No.: WO2013/068255
PCT Pub. Date: May 16, 2013

(65) Prior Publication Data
US 2014/0322283 A1    Oct. 30, 2014

(30) Foreign Application Priority Data

Nov. 10, 2011  (EP) .................................. 11188600
Feb. 21, 2012  (EP) .................................. 12156387

(51) Int. Cl.
| | | |
|---|---|---|
| *A61L 9/12* | (2006.01) |
| *A61K 8/11* | (2006.01) |
| *A61Q 5/00* | (2006.01) |
| *B01J 13/14* | (2006.01) |
| *C11D 3/50* | (2006.01) |
| *C11D 17/00* | (2006.01) |
| *A61Q 13/00* | (2006.01) |
| *A61K 8/84* | (2006.01) |
| *A61K 8/06* | (2006.01) |
| *A61K 8/41* | (2006.01) |
| *A61L 9/012* | (2006.01) |
| *A61Q 19/00* | (2006.01) |
| *C11B 9/00* | (2006.01) |

(52) U.S. Cl.
CPC . *A61K 8/11* (2013.01); *A61K 8/062* (2013.01); *A61K 8/416* (2013.01); *A61K 8/84* (2013.01); *A61L 9/012* (2013.01); *A61Q 5/00* (2013.01); *A61Q 13/00* (2013.01); *A61Q 19/00* (2013.01); *B01J 13/14* (2013.01); *C11B 9/00* (2013.01); *C11D 3/505* (2013.01); *C11D 17/0039* (2013.01); *A61K 2008/115* (2013.01); *A61K 2800/30* (2013.01); *A61K 2800/412* (2013.01)

(58) Field of Classification Search
CPC ... A61K 2800/412; A61K 8/11; A61K 8/062; C11D 3/505; C11D 17/0039; A61L 27/26; A61Q 13/00; A61Q 19/10; A61Q 19/00; A61Q 5/00; A61Q 15/00; B01F 13/0059
USPC ......... 428/402–402.24, 403, 404, 407, 321.1, 428/474.4; 424/400, 408, 450, 451, 455, 424/93.7, 184.1, 497, 489, 501, 490, 491, 424/492, 493, 494, 495; 264/534, 5, 41, 264/4–4.7; 427/331, 389.9, 212, 427/213–213.36, 483, 256
See application file for complete search history.

(56) References Cited

U.S. PATENT DOCUMENTS 5,691,426 A    11/1997  Floyd

FOREIGN PATENT DOCUMENTS

| EP | 1065227 A2 | 1/2001 |
|---|---|---|
| WO | WO2006129252 A2 | 12/2006 |
| WO | WO2008098387 A1 | 8/2008 |
| WO | WO2009100553 A1 | 8/2009 |
| WO | WO2011161618 A1 | 12/2011 |

OTHER PUBLICATIONS

International Search Report + Written opinion, application PCT/EP2102/071340, filed on Oct. 29, 2012.

*Primary Examiner* — James J Seidleck
*Assistant Examiner* — S. Camilla Pourbohloul
(74) *Attorney, Agent, or Firm* — Winston & Strawn LLP

(57) ABSTRACT

The present invention relates to water-dispersible core-shell microcapsules essentially free of formaldehyde. In particular it concerns core-shell microcapsules having a shell obtained by reacting polyisocyanates or polyoxirans cross-linkers and oligomeric compositions which are the reaction products between a polyamine component and a particular mixture of glyoxal and a $C_{4-6}$ 2,2-dialkoxy-ethanal. The present invention comprises also the invention's core-shell microcapsules as part of a perfuming composition or of a perfuming consumer product.

9 Claims, No Drawings

STABLE FORMALDEHYDE-FREE MICROCAPSULES

TECHNICAL FIELD

The present invention relates to the field of perfumery. More particularly, it concerns water-dispersible core-shell microcapsules essentially free of formaldehyde.

The present invention comprises also the invention's core-shell microcapsules as part of a perfuming composition or of a perfuming consumer product.

PRIOR ART

Microcapsules are a widely known type of products, generally used as carrier of a liquid phase.

A specific type of said microcapsules is the so-called aminoplast microcapsules comprising an external wall obtained by reacting a polyamine (in general melamine, i.e. 2,4,6-triamino-1,3,5-triazine) and an aldehyde (almost always in fact formaldehyde). These microcapsules are very useful in the case where the liquid core is a volatile compound or composition, like perfumes, since they are able to break under certain conditions liberating the volatile in a controlled manner.

However said capsules, which are essentially formaldehyde based, contain always residual amounts of free formaldehyde due to unreacted precursors or a slow decomposition of the thermoset oligomers. Capsules which are formaldehyde-free are nowadays desired due to regulatory concerns, therefore there is a need by the industry for formaldehyde free core-shell microcapsules possessing performance similar to the formaldehyde based ones, which have the best performance in stability and product delivery.

Some attempts to obtain formaldehyde free microcapsules have been published in the prior art. One may mention the ones disclosed in WO 2009/100553 describing aminoplast capsules obtained by reacting at least a polyamine and unclearly defined "substituted methylene moieties" which are exemplified by hemi-acetal of glyoxal esters or by 2,2-dimethoxy-ethanal (DME) or 2,2-diphenoxy-ethanal. In the facts, all capsules concretively described are obtained by reacting melamine (as unique polyamine) and DME or methyl 2-hydroxy-2-methoxy-acetate as "substituted methylene moieties". However we found that the performances and stability of such capsules are not satisfactory for an industrial application, as shown further below in the Examples.

Therefore there is still a need for core-shell microcapsules formaldehyde-free and having superior stability performances.

DESCRIPTION OF THE INVENTION

We have now surprisingly discovered a new type of formaldehyde-free microcapsules which have superior stability compared to the prior art formaldehyde-free core-shell microcapsules of similar constitution.

Therefore, a first object of the present invention is a process for obtaining the above microcapsules. In other words, a process for the preparation of a core-shell microcapsule, said process comprising the steps of:
1) preparing an oligomeric composition comprising the reaction product of, or obtainable by reacting together:
   a) a polyamine component in the form of melamine or of a mixture of melamine and at least one $C_{1-4}$ compound comprising two $NH_2$ functional groups;
   b) an aldehyde component in the form of a mixture of glyoxal, a $C_{4-6}$ 2,2-dialkoxy-ethanal and optionally a glyoxalate, said mixture having a molar ratio glyoxal/$C_{4-6}$ 2,2-dialkoxy-ethanal comprised between about 1/1 and 10/1; and
   c) a protic acid catalyst;
2) preparing an oil-in-water dispersion, wherein the droplet size is comprised between 1 and 600 µm, and comprising:
   i) an oil;
   ii) a water medium;
   iii) at least an oligomeric composition as obtained in step 1);
   iv) at least a cross-linker selected amongst:
      A) $C_4$-$C_{12}$ aromatic or aliphatic di- or tri-isocyanates and their biurets, triurets, trimers and trimethylol propane-adduct; and/or
      B) a di- or tri-oxiran compounds of formula

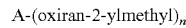

wherein n stands for 2 or 3 and A represents a $C_2$-$C_6$ group optionally comprising from 2 to 6 nitrogen and/or oxygen atoms;
   v) optionally a $C_{1-4}$ compound comprising two $NH_2$ functional groups;
3) heating said dispersion;
4) cooling said dispersion; and
5) optionally adding to the dispersion of step 4) at least one cationic polymer and/or urea or ethylene urea; and
6) optionally drying the final dispersion to obtain the dried core-shell microcapsule.

For the sake of clarity, by the expression "core-shell microcapsule", or the similar, in the present invention it is meant that the capsule has a size in the micron range (e.g. a mean diameter comprised between about 1 and 600 µm) and comprises an external solid oligomers-based shell or wall and an internal continuous oil phase enclosed by the external shell. In other words bodies like coacervates or extrudates (i.e. porous solid phases containing droplets of a liquid) are not part of the invention. According to an embodiment of the invention, the size of said microcapsules, and consequently of the droplet size in step 1), is comprised between about 5 and 200 µm.

For the sake of clarity, by the expression "dispersion", in the present invention it is meant a system in which particles are dispersed in a continuous phase of a different composition and specifically includes a suspension or an emulsion.

According to any one of the above embodiments of the present invention, the dispersion comprises between about 10% and 50% of oil, percentage being expressed on a w/w basis relative to the total weight of the dispersion. In still another aspect of the invention, the dispersion comprises between about 20% and 45% of oil.

By "oil" we mean here an organic phase that is a liquid at about 20° C. and which will be in the core of the core-shell capsules. According to any one of the above embodiments of the present invention, said oil can be selected amongst a perfume, insecticide, malodor counteracting substance, fungicide, insect repellent, and the mixtures thereof.

According to any one of the above embodiments of the present invention, said oil is a perfume. Said perfume can be in the form of a pure perfuming ingredient or of a perfuming composition.

By "perfuming composition" it is meant here the normal meaning of the art, i.e. a composition comprising several perfuming ingredients and optionally at least one suitable solvent and/or at least one perfumery adjuvant.

By "perfuming ingredient" or "perfuming co-ingredient" it is meant here a compound which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "suitable solvent" we mean here a material which is practically neutral from a perfumery point of view, i.e. that does not significantly alter the organoleptic properties of perfuming ingredients and is generally not miscible with water, i.e. possesses a solubility in water below 10%, or even below 5%. Say solvent is in general a solvent commonly used in perfumery, such as for example dipropyleneglycol, diethyl phthalate, isopropyl myristate, benzyl benzoate, 2-(2-ethoxyethoxy)-1-ethanol or ethyl citrate, limonene or other terpenes, isoparaffins such as those known under the trademark Isopar® (origin: Exxon Chemical) or glycol ethers and glycol ether esters such as those known under the trademark Dowanol® (origin: Dow Chemical Company).

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

According to any one of the above embodiments of the present invention, the water medium comprises, or is essentially, water, as a diluent of the dispersion, and optionally may comprise at least a polyol and/or at least a stabilizer.

According to any one of the above embodiments of the present invention, the dispersion comprises between about 0% and 5% of at least a stabilizer, percentage being expressed on a w/w basis relative to the total weight of the dispersion. In still another aspect of the invention, the dispersion comprises between about 0% and 2% of at least a stabilizer. In still another aspect of the invention, the dispersion comprises between about 0% and 1% of at least a stabilizer. In the case where the aldehyde component comprises also a glyoxalate, and in particular when the diamino compound is 1H-1,2,4-triazole-3,5-diamine, comprises the amount of said stabilizer in the dispersion could be 0% (no addition of stabilizer).

For the sake of clarity, in the present context, by the expression "stabilizer", or the similar, it is meant the normal meaning understood by a person skilled in the art, i.e. a compound that is capable of, or is added to, stabilize the system, e.g. to prevent aggregation or agglomeration of the microcapsules, for example in the application or during their preparation. The use of said stabilizer is standard knowledge of the person skilled in the art.

For the purpose of the present invention, said stabilizer can be a ionic or non-ionic surfactant or a colloidal stabilizer. The exact nature of such stabilizers is well known by a person skilled in the art. As non limiting examples, one may cite the followings stabilizers: non-ionic polymers such as polyvinyl alcohol, cellulose derivatives such hydroxyethyl cellulose, polyethylene oxide, co-polymers of polyethylene oxide and polyethylene or polypropylene oxide, co-polymers alkyl acrylates and N-vinylpyrrolidone;

ionic polymers such as co-polymers of acrylamide and acrylic acid (such as Alcapsol® 144 from Ciba), e.g. acid/acrylamide copolymers produced from monomer mixture of acrylic acid and acrylamide wherein the acrylic acid content is in the range of from 30 to 70%, acid anionic surfactant (such as sodium dodecyl sulfate), acrylic co-polymers bearing a sulfonate group (such as sodium poly(styrene sulfonate), and co-polymers of vinyl ethers and maleic anhydride.

According to any one of the above embodiments of the present invention, said stabilizer is a ionic surfactant.

According to any one of the above embodiments of the present invention, the dispersion comprises also between about 0% and 10% of at least a polyol, percentage being expressed on a w/w basis relative to the total weight of the dispersion, or even comprised between about 0% and 2% of at least a polyol. In still another aspect of the invention, when the diamino compound is urea, said amount can be comprised between about 0.1% and 2% of at least a polyol. In still another aspect of the invention, when the diamino compound is 1H-1,2,4-triazole-3,5-diamine, said amount can be comprised between about 0% and 1.5% or 0.5% of at least a polyol.

For the sake of clarity, by the expression "polyol", or the similar, it is meant the normal meaning understood by a person skilled in the art, i.e. a compound comprising one or more alcohol functional groups and is generally used to help the reticulation/curing/deposition of the microcapsule's shell. The use of said polyol is standard knowledge of the person skilled in the art.

Said polyol may be selected from aromatic, aliphatic and polymeric polyols. As non-limiting examples, one may cite aromatic polyols such as 3,5-dihydroxy toluene, resorcinol, xylenol, bisphenol, polyhydroxy naphthalene, polyphenol obtained by the degradation of cellulose; aliphatic polyols such as humic acids, 2,2,-dimethyl-1,3-propane diol, 1,1,1-tris-(hydroxymethyl)-propane, pentaerythritol, sorbitol or sugar derivatives and the similar; polymeric polyols such as celluloses or carboxymethyl cellulose derivatives such as alkaline salts of carboxymethyl cellulose (e.g. and in particular a sodium salt like Ambergum® 1221 (from HERCULES AQUALON) or Blanose™ 12M8P (from Ashland Inc.).

According to any one of the above embodiments of the present invention, said polyol is an aliphatic polymeric polyol such as a carboxymethyl ether cellulose derivative (such as, and in particular, Ambergum® 1221 or Blanose™ 12M8P).

According to any one of the above embodiments of the present invention, the dispersion comprises between about 1% and 20% of oligomeric composition, percentage being expressed on a w/w basis relative to the total weight of the dispersion. In still another aspect of the invention, the dispersion comprises between about 1% and 8% of oligomeric composition. In general the amount of oligomeric composition present in the dispersion can also be defined as being comprised between 4% and 15% of oligomeric composition on a w/w basis relative to the total weight of oil added in the dispersion.

Said oligomeric compositions are described in patent application WO 2011/161618. However, for sake of completeness, said oligomeric composition may be in particular as described herein below.

The term "glyoxal" is understood to mean both the free di-aldehyde form (i.e. OHC—CHO) and the hydrated form (e.g. $(HO)_2HC$—CHO).

The term "glyoxalate" is understood to mean the glyoxalic acid or an alkaline salt of glyoxalic acid (such as OHC—COONa or OHC—COOK) or mixture thereof. The term "glyoxalate" is also understood to mean both the free aldehyde form (i.e. OHC—COOH) and the hydrated form (e.g. $(HO)_2HC$—COOH or $(HO)_2HC$—COONa).

For the sake of clarity, by the expression "an oligomeric composition", or the similar, it is meant the normal meaning understood by a person skilled in the art, i.e. a mixture of oligomers, as reaction product, and other optional components. In the simplest embodiment of the invention, said optional embodiment can be, as non-limiting example, water and/or unreacted reagent of the process (e.g. the acid catalyst). By "oligomer" it is meant a compound which is not itself a macropolymer, as is a resin, but rather a small size molecule comprising between about 4 to 100, or even preferably 30, units derived from the monomeric constituents.

According to any one of the above embodiments of the present invention, the invention's oligomers possess a molecular weight (MW) comprised between about 200 g/mol and 2500 g/mol. In still another aspect of the invention, said MW is comprised between about 220 g/mol and 1200 g/mol.

According to any one of the above embodiments of the present invention, as polyamine component it is used a mixture of melamine and at least one $C_{1-4}$ compound comprising two $NH_2$ functional groups. According to any one of the above embodiments of the present invention, said compound is a $C_{1-2}$ compound comprising two $NH_2$ functional groups. For the sake of clarity, by the expression "$C_{1-4}$ compound comprising two $NH_2$ functional groups", or the similar, it is meant a $C_{1-4}$ hydrocarbon compound comprising two $NH_2$ functional groups, and additionally said compound may optionally comprise from one to three nitrogen and/or oxygen atoms. In particular said compound is a $C_{1-2}$ compound comprising two $NH_2$ functional groups and a carbonyl or a 1,2,4-triazole functional group. Non-limiting examples of said $C_{1-4}$ compound comprising two $NH_2$ functional groups (diamino compound) can be urea, 1H-1,2,4-triazole-3,5-diamine and mixtures thereof.

According to any one of the above embodiments of the present invention, it can be used mixtures with a molar ratio melamine/diamino compound comprised between about 4/1 and 1/4, or even comprised between about 3.5/1 and 1/3.5, or alternatively between about 2/1 and 1/3, or alternatively between about 1.3/1 and 1/3. In the case where the diamino compound is 1H-1,2,4-triazole-3,5-diamine, one may also mention molar ratio melamine/1H-1,2,4-triazole-3,5-diamine comprised between about 1.5/1 and 1/1.5.

For the sake of clarity, by the expression "$C_{4-6}$ 2,2-dialkoxyethanal" it is meant a 2,2-dialkoxyethanal having in total from 4 to 6 carbon atoms. According to an embodiment of the present invention, said $C_{4-6}$ 2,2-dialkoxyethanal can be 2,2-dimethoxy-ethanal, 2,2-diethoxy-ethanal and mixtures thereof.

According to any one of the above embodiments of the present invention, said aldehyde component has a molar ratio glyoxal/2,2-dialkoxy-ethanal comprised between about 1.1/1 and 7/1, or even comprised between about 1.4/1 and 6.5/1. One may also mention that in the case where the diamino compound is urea, then said glyoxal/2,2-dialkoxy-ethanal may advantageously be comprised between about 1.5/1 and 6.1/1. One may also mention that in the case where the diamino compound is 1H-1,2,4-triazole-3,5-diamine, then said glyoxal/2,2-dialkoxy-ethanal may advantageously be comprised between about 1.4/1 and 2.2/1.

The aldehyde component may also include (as optional constituent) a glyoxalate. According to any one of the above embodiments of the present invention, when present, said glyoxalate is present in amounts such that molar ratio glyoxal/glyoxalate is comprised between about 4/1 and 1/1, or even comprised between about 3.5/1 and 2/1. According to any one of the above embodiments of the present invention, said glyoxalate is present and within amounts such as stated in the ratio mentioned above, in particular when the diamino compound is 1H-1,2,4-triazole-3,5-diamine.

According to any one of the above embodiments of the present invention, the said polyamine component and the aldehyde component are admixed in a ratio such that the molar ratio of total amine functional group/total free aldehyde functional group (also referred as $(NH_2)_{tot}/(CHO)_{tot}$) is comprised between about 4/1 and 1/2, or even comprised between about 1.9/1 and 1/1.9, or alternatively between about 1.7/1 and 1/1.7. For the purpose of clarity, a melamine accounts for 3 amine functional groups and the diamino compound, e.g. urea, for 2. Similarly glyoxal accounts for 2 free aldehyde functional groups and the $C_{4-6}$ 2,2-dialkoxy-ethanal or the glyoxalate accounts for 1 free aldehyde functional group.

As a person skilled in the art understands and knows, said protic acid is a catalyst or initiator of the oligomerisation, and therefore said protic acid may react also with the other components and becoming, at least partially, part of the oligomers formed. According to any one of the above embodiments of the present invention, said protic acid catalyst is selected amongst mineral acids, $C_{1-6}$ mono or dicarboxylic acids and mixtures thereof. Non-limiting examples of such acids are phosphoric, nitric, sulfuric or hydrochloric acids, or acetic, formic, oxalic or glyoxilic acids. More specifically, said acid catalyst is selected amongst formic, acetic, glyoxylic and nitric acids and mixtures thereof.

According to any one of the above embodiments of the present invention, the oligomeric composition is obtained by reacting the various components in water and the oligomeric composition is obtained by a single step process wherein all reagents are mixed together or by a multistep process wherein the reagents are reacted together subsequently.

According to any one of the above embodiments of the present invention, the oligomer is obtained by a process where all the various components are reacted together in water, and the pH of the final reaction medium is preferably comprised between 6 and 9.5.

According to any one of the above embodiments of the present invention, the oligomer is obtained by a two-step process. In a first step, the polyamine component is reacted with the aldehyde component in an aqueous medium, at a basic pH. Then in a second step, there is added to the reaction medium the acid catalyst, so as to work at an acidic pH.

According to any one of the above embodiments of the present invention, the pH of said first step can be comprised between about 7 and 10, or even between about 8.5 and 10. In still another aspect of the invention, the temperature of reaction of the first step can be comprised between about 20° C. and 80° C., or even between about 40° C. and 80° C.

In still another aspect of the invention, said first step can be carried out for about 0.1 hour to about 4 hours (reaction time). However, more specifically, the reaction time of said first step depends on the temperature of the reaction, and its pH and can be comprised, for example, between about 1 hour to about 4 hours, for a temperature comprised between about 40° C. and about 80° C. and a pH between about 8 and about 10. Alternatively said reaction time can be comprised, for example, between about 0.5 hour to about 2 hours, for a temperature comprised between about 50° C. and about 80° C. and a pH between about 7 and about 9.5.

The pH of said first step can be typically set up by adding to the reaction medium an adequate amount of potassium or sodium hydroxide.

According to any one of the above embodiments of the present invention, the said acid catalyst is added to the reaction mixture of the first step in an amount sufficient to acidify the latter. The pH of said second step can be comprised between about 4.0 and 6, or even between about 4.5 and 5.5. In still another aspect of the invention, the temperature of reaction of the first step can be comprised between about 40° C. and 100° C., or even between about 50° C. and 90° C.

In still another aspect of the invention, said second step can be carried out for about 0.5 hour to about 4 hours (reaction time). However, more specifically, the reaction time of said first step depends on the temperature of the reaction, and its pH and can be comprised, for example, between about 1 hour to about 2.5 hours, for a temperature comprised between about 50° C. and about 80° C. and a pH between about 4.5 and about 5.5. Alternatively said reaction time can be comprised, for example, between about 0.5 hour to about 4 hours, for a temperature comprised between about 50° C. and about 80° C. and a pH between about 4.5 and about 5.5.

As can be noticed, the result of such process is an aqueous solution comprising the invention's oligomeric composition. Typically, the aqueous solution comprises between about 30% and 70% of oligomeric composition (solid content), percentage being expressed on a w/w basis relative to the total weight of the solution.

Said aqueous solution can be used directly for the process of preparation of the microcapsules, as described further below, or can be dried to provide the oligomeric composition.

The dispersion of step 2) comprises also at least a cross-linker which can be a di- or tri-isocyanates (herein after also referred to as a polyisocyanate) and/or an oxirane based compound (herein after also referred to as a polyoxiran).

According to any one of the above embodiments of the present invention, the dispersion comprises between about 0.5% and 15% of at least a cross-linker, percentage being expressed on a w/w basis relative to the total weight of the dispersion, or even comprised between about 1% and 12% of at least a cross-linker.

For the sake of clarity by "aromatic or aliphatic di- or tri-isocyanates" it is meant here a hydrocarbon compound, which can be totally aliphatic or comprising also an aromatic group, and which also possesses two or three isocyanate groups.

For the sake of clarity, by "biuret, triuret" it is meant here a self-addition product of such aromatic or aliphatic di- or tri-isocyanates and which comprise the tri-radical HN—CO—N—CO—NH (biuret functional group) or the tetra-radical HN—CO—N—CO—N—CO—NH (triuret functional group). Said biurets or triurets are generally products of reaction of water with a di or tri-isocyanate. Similarly, by "trimer" it is meant here an isocyanurate derivative of said di- or tri-isocyanates (i.e. a compound comprising the moiety 1,3,5-triazinane-2,4,6-trione). By "trimethylol propane-adduct" it is meant here an isocyanate which is a reaction product between the di- or tri-isocyanate and trimethylol propane.

According to any one of the above embodiments of the present invention, one can mention the following di- or thi-isocyanates: hexamethylene diisocyanate, isophorone diisocyanate, xylylene diisocyanate, toluene diisocyanate, a trimethylol propane-adduct of toluene diisocyanate (commercially available from Bayer under the tradename Desmodur® L75), a trimethylol propane-adduct of xylylene diisocyanate (commercially available from Mitsui Chemicals under the tradename Takenate® D-110N), a trimer of hexamethylene diisocyanate, a trimer of isophorone diisocyanate, a trimethylol propane-adduct of hexamethylene diisocyanate (available from Mitsui Chemicals) or a biuret of hexamethylene diisocyanate (commercially available from Bayer under the tradename Desmodur® N 100).

According to any one of the above embodiments of the present invention, one can mention the following oxiran-2-ylmethyl derivatives: 1,3,5-tris(oxiran-2-ylmethyl)-1,3,5-triazinane-2,4,6-trione, 4-(oxiran-2-ylmethoxy)-N,N-bis(oxiran-2-ylmethyl)aniline, 1,3-bis(oxiran-2-ylmethoxy)benzene (also known as resorcinol diglycidylether), 1,2-bis(oxiran-2-ylmethoxy)ethane (also known as ethyleneglycol diglycidylether) and 2,2'-(2-ethyl-2-((oxiran-2-ylmethoxy)methyl)propane-1,3-diyl)bis(oxy)bis(methylene)dioxirane (also known as trimethylolpropane triglycidylether).

According to any one of the above embodiments of the present invention, the cross linker is a di- or tri-isocyanate.

According to the invention's process, the dispersion may comprise also a $C_{1-4}$ compound comprising two $NH_2$ functional groups (diamino compound) as defined above. It is believed that said compound helps the hardening of the microcapsule shell. The addition of said compound can be attractive in particular when there is used an oligomer wherein the $NH_{2tot}/CHO_{tot}$ ratio is close to the minimum of the range specified above.

According to any one of the above embodiments of the invention's process, the dispersion of step 2) does comprise said $C_{1-4}$ compound comprising two $NH_2$ functional groups. Said $C_{1-4}$ compound comprising two $NH_2$ functional groups (diamino compound) can be urea, 1H-1,2,4-triazole-3,5-diamine and mixtures thereof.

According to any one of the above embodiments of the invention, in step 2) there is added an amount of diamino compound comprised between about 5% and 100%, or even between about 10% and 80%, or alternatively between about 15% and 75%, percentage being expressed on a w/w basis relative to the total weight of the resin. It is clearly understood by a person skilled in the art that only part of said added diamino compound will be incorporated into the microcapsule shell.

Typical manners to form the dispersions of step 2) are known by a person skilled in the art, and are also described herein below or in the Examples below. Typically, the dispersion can be obtained by stirring the components up to 24000 rpm to disperse oil in water (with mechanical stirrer, ultra Turrax or microwave).

According to any one of the above embodiments of the present invention, the pH of said dispersion can be set between 4 and 9.5, prior to step 3), for example by adding an appropriate amount of a base such as sodium hydroxide.

According to any one of the above embodiments of the invention, in step 3) the dispersion is heated at a temperature comprised between 35° C. and 100° C. In still another aspect of the invention, the temperature of said emulsion of dispersion is comprised between 50° C. and 90° C. Said thermal treatment may be carried on for between about 0.5 hour and 6 hours. More specifically, the time of heating depends on the temperature and the pH of said emulsion or dispersion, and for example can be comprised between about 1 hour to about 5 hours, for a temperature comprised between about 60° C. and about 80° C. and a pH between about 4.5 and about 9.5.

Step 4) of the invention's process is meant to stop the process of hardening of the shell of the thus obtained core-shell microcapsule, and can be performed by any known method. Typically, the dispersion can be cooled at temperatures comprised between about 10° and 30° C., in general to room temperature. Said step 4) may optionally include a neutralization of the thus obtained dispersion at a pH comprised between pH between 6.5 and 7.5, for example by adding an appropriate amount of a base such as sodium hydroxide.

According to optional step 5), one may also add to the invention's dispersion some cationic polymers. Preferred cationic polymers will have cationic charge densities of at least 0.5 meq/g, more preferably at least about 1.5 meq/g, but also preferably less than about 7 meq/g, more preferably less than about 6.2 meq/g. The cationic charge density of the cationic polymers may be determined by the Kjeldahl method as described in the US Pharmacopoeia under chemical tests for Nitrogen determination.

The preferred cationic polymers are chosen from those that contain units comprising primary, secondary, tertiary and/or quaternary amine groups that can either form part of the main polymer chain or can be borne by a side substituent directly connected thereto. The weight average (Mw) molecular weight of the cationic polymer is preferably between 10,000 and 2M Dalton, more preferably between 50,000 and 1.5M Dalton. As specific examples, one may cite Salcare® SC60 (cationic copolymer of acrylamidopropyltrimonium chloride and acrylamide, origin: BASF) or Luviquat®, such as the PQ 11N, FC 550 or Supreme (polyquaternium-11 to 68 or quaternized copolymers of vinylpyrrolidone origin: BASF), or also the Jaguar® (C13S or C17, origin Rhodia).

According to any one of the above embodiments of the invention, in step 5) there is added an amount of cationic polymers comprised between about 0% and 60%, or even between about 5% and 40%, percentage being expressed on a w/w basis relative to the total weight of the resin. It is clearly understood by a person skilled in the art that only part of said added cationic polymers will be incorporated into/deposited on the microcapsule shell.

According to optional step 5), one may also add to the invention's dispersion an amount of urea or ethylene urea which can be useful to scavenge possible free glyoxal in the slurry. According to any one of the above embodiments of the invention, in step 5) there is added an amount of urea or ethylene urea comprised between about 0% and 10%, or even between about 1% and 5%, percentage being expressed on a w/w basis relative to the total weight of the dispersion. It is clearly understood by a person skilled in the art that only part of said added cationic polymers will be incorporated into/deposited on the microcapsule shell.

As noticed above, the result of such process is an aqueous dispersion (or slurry) comprising the invention's core-shell microcapsules. Typically, the aqueous slurry comprises between 10% and 60% of capsules, percentage being expressed on a w/w basis relative to the total weight of the slurry. According to any one of the above embodiments of the invention, the aqueous slurry comprises between 20% and 55% of capsules.

Said aqueous slurry can be used directly as perfuming ingredient, in particular for applications which are aqueous based, e.g. a softener or a liquid soap. Therefore another object of the present invention is an aqueous slurry comprising the invention's microcapsules, for example a slurry as obtained directly for the process of preparation of the microcapsules. Said slurry may further comprise some formulation aids, such as stabilizer or viscosity control agents, or even biocides or bactericides.

Alternatively, the slurry obtained by the process described above can be submitted to a drying, like spay drying, to provide the microcapsules as such, i.e. in a powdery form. It is understood that any standard method known by a person skilled in the art to perform such drying is also applicable.

For the reasons set above, another object of the present invention is a composition of matter as obtained, or obtainable, by the above-described process. It is understood by a person skilled in the art that said composition of matter comprises the core-shell microcapsules in the dry form or as a water-suspension.

According to any one of the above embodiments of said core-shell microcapsules, the amount of the core of oil accounts typically between 40% and 98% of the total weight of the microcapsules (i.e. the weight of the dispersion minus the weight of water). In still another aspect of the invention, said core of oil accounts between 70% and 95%, or even between 80% and 90%, of the total weight of the microcapsules.

According to any one of the above embodiments of said core-shell microcapsules, the amount of the shell accounts typically between 2% and 60% of the total weight of the capsules. In still another aspect of the invention, said oligomers-based shell accounts between 5% and 30%, or even between 10% and 20%, of the total weight of the microcapsules.

According to any one of the above embodiments of the invention, said core-shell microcapsules are those obtained by using in the invention's process an oil-in-water dispersion wherein the oil is a perfume oil and comprising
    at least an oligomeric composition as defined above and comprising a glyoxalate;
    a cross-linker, as defined above;
    optionally at least a polyol, as defined above;
and wherein there is added during the process also at least a $C_{1-4}$ compound comprising two $NH_2$ functional groups, as defined above (step 2 of the invention's process), i.e. a process providing microcapsules capsules comprising glyoxalate and not comprising a stabilizer.

As mentioned above, the invention concerns the use of an invention's microcapsule as perfuming ingredient. In other words, it concerns a method to confer, enhance, improve or modify the odor properties of a perfuming composition or of a perfumed article, which method comprises adding to said composition or article an effective amount of at least an invention's microcapsule. By "use of an invention's microcapsule" it has to be understood here also the use of any composition containing an invention's microcapsule and which can be advantageously employed in perfumery industry.

Said compositions, which in fact can be advantageously employed as perfuming ingredients, are also an object of the present invention.

Therefore, another object of the present invention is a perfuming composition comprising:
i) as perfuming ingredient, at least one invention's microcapsule, or a slurry containing said invention's microcapsule, as defined above;
ii) at least one ingredient selected from the group consisting of a liquid perfumery carrier and a perfumery base; and
iii) optionally at least one perfumery adjuvant.

By "perfumery carrier" we mean here a liquid material which is practically neutral from a perfumery point of view, i.e. which does not significantly alter the organoleptic properties of perfuming ingredients.

As perfumery carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers, than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

By "perfumery base" we mean here a composition comprising at least one perfuming co-ingredient, as defined above. The expression "perfumery adjuvant" is as defined above.

An invention's composition consisting of at least one invention's microcapsule and at least one perfumery carrier represents a particular embodiment of the invention as well as a perfuming composition comprising at least one invention's microcapsule, at least one perfumery carrier, at least one perfumery base, and optionally at least one perfumery adjuvant.

It is useful to mention here that the possibility to have, in the compositions mentioned above, more than one invention's microcapsule is important as it enables the perfumer to prepare accords, perfumes, possessing the odor tonality of various compounds of the invention, creating thus new tools for his work.

Furthermore, the invention's core-shell microcapsules can also be advantageously used in all the fields of modern perfumery, i.e. fine or functional perfumery, to positively impart or modify the odor of a consumer product into which said invention's microcapsules are added. Consequently, a perfuming consumer product which comprises:
i) as perfuming ingredient, at least one invention's microcapsule, as defined above; and
ii) a perfumery consumer base;
is also an object of the present invention.

The invention's compound can be added as such or as part of an invention's perfuming composition.

For the sake of clarity, it has to be mentioned that, by "perfuming consumer product" it is meant a consumer product which is expected to deliver at least a perfuming effect, in other words it is a perfumed consumer product. For the sake of clarity, it has to be mentioned that, by "perfumery consumer base" we mean here the functional formulation, as well as optionally additional benefit agents, corresponding to a consumer product which is compatible with perfuming ingredients and is expected to deliver a pleasant odor to the surface to which it is applied (e.g. skin, hair, textile, or home surface). In other words, a perfuming consumer product according to the invention comprises the functional formulation, as well as optionally additional benefit agents, corresponding to the desired consumer product, e.g. a detergent or an air freshener, and an olfactive effective amount of at least one invention's microcapsule.

The nature and type of the constituents of the perfumery consumer base do not warrant a more detailed description here, which in any case would not be exhaustive, the skilled person being able to select them on the basis of his general knowledge and according to the nature and the desired effect of said product.

Non-limiting examples of suitable perfumery consumer base can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent.

According to an embodiment of the invention, the fine or functional perfumery base is in the form of a fabric, home, or hair care product, such as a fabric softener, a detergent or a shampoo.

The proportions in which the microcapsules according to the invention can be incorporated into the various aforementioned articles or compositions vary within a wide range of values. These values are dependent on the nature of the article to be perfumed and on the desired organoleptic effect as well as the nature of the co-ingredients in a given base when the microcapsules according to the invention are mixed with perfuming co-ingredients, solvents or additives commonly used in the art.

For example, in the case of perfuming compositions, typical concentrations are in the order of 0.1% to 50% by weight, or even more, of the microcapsules of the invention based on the weight of the composition into which they are incorporated. Concentrations lower than these, such as in the order of 0.01% to 5% by weight, can be used when these microcapsules are incorporated into perfumed articles, percentage being relative to the weight of the article.

EXAMPLES

The invention will now be described in further detail by way of the following examples, wherein the abbreviations have the usual meaning in the art, the temperatures are indicated in degrees centigrade (° C.).
TGA:
Solid content of resins was measured with a thermogravimetric analyser (Mettler-Toledo TGA/SDTA851$^e$) equipped with a microbalance (accuracy: 1 µg) and an accurate oven having an internal volume of 35 ml, under a constant nitrogen flow of 20 ml/min. Resin (10 mg) was introduced in aluminium pan of 40 µl. The measurement started from 25° C. to 100° C. at 5° C./min, staid at 100° C. for 1 h, and finally to 200° C. at 10° C./min. The solid content was determined by doing the ratio between weight of sample (plateau) and the initial weight in the crucible.

Capsule performance was assessed at 50° C., and 280° C. or 300° C. with a similar thermogravimetric analyser. Perfume evaporation was measured as a function of time. Microcapsules dispersion (10 mg) was introduced in alumina pan of 70 µl. The measurement at 50° C. started from 25° C. to 50° C. at 5° C./min, and then staid at 50° C. for 4 h. The measurement at 280° C. started from 25° C. to 280° C. at 5° C./min, and then staid at 280° C. for 1 h and 5 min. The measurement at 300° C. started from 25° C. to 300° C. at 5° C./min, and then staid at 300° C. for 1 h. A slower evaporation of the perfume oil with a long-lasting profile was related to a more stable capsule.

TOF-MS:

The analysis of the resin compositions was carried out by liquid chromatography, with a TOF-MS detector (TOF High Resolution >10000, Agilent 1200 HPLC system Agilent G1969A MS TOF system composed of a Multimode source APCI+ESI) composed of a binary solvent manager (or pump G1312b), and an Auto sampler (g1329a). This TOF detector can analyze product having molecular weight up to 3000 g/mol. Analyses were carried out in formic acid aqueous solution at 0.1 wt % at RT without columns. Method Standard: Water premix: Acid formic 0.1% (Biosolve no 23244125 ULC/MSD lot 550361). HPLC: 0.5 ml/min, injection volume: 1 µl with welplate sampler (without column), temperature of thermostat: 60° C. (+/−0.1° C.). One blank run was performed between each sample.

MSD:

Multi mode Electro spray (ESI)+APCI Pos LCMSD TOF High Resolution 3 ppm acq. Source: Mode Positive, Charging Voltage 2000 V, V cap 2500 V, Corona 4 µA, drying gas $N_2$, 5 l/min at 325° C., nebuliser 30 psig at 200° C. Fragmentor: 140 to 320 V. Scan range: 103 to 3000, online standard for mass adjustment.

SEC:

Solutions of resins (0.5 wt %) were analyzed by size exclusion chromatography in formic acid 0.1 wt % and ammonium acetate 0.05M aqueous solution (mobile phase, pH=4.70). Analyses were carried out at 30° C. with a flow of 0.45 ml/min, by using a ThermoFinnigan Surveyor LC-Pump and Autosampler (20 µL injected). The column used was supplied by TOSOH BIOSCIENCE (TSKgel Super AW2500 6.0 mm ID, 15.0 cm L, polyvinyl resin). Molecular weights were measured by using ThermoFinnigan Surveyor UV/VIS detector and a SpectraSystem RI-150 refractive index detector (35° C.). Detectors were calibrated with standard poly (ethylene glycol) from 106 to 1982 g/mol.

Materials:

2,2-dimethoxyethanal (DME), oxalaldehyde (glyoxal, GY), and 2-oxoacetic acid (glyoxylic acid, AGY) were used as aqueous solutions at 60%, 40% and 50% w/w, respectively. 1,3,5-triazine-2,4,6-triamine (Melamine, M), urea and 1H-1, 2,4-triazole-3,5-diamine (guanazole, T, purity=88.6%) were used as received. Ambergum® 1221 was used as a solution at 2% w/w in water. Alcapsol 144 was dissolved in water at 20% w/w. Sodium hydroxide (NaOH) was dissolved in water at 30% w/w. Nitric acid was used as a solution at 30% w/w in water. Formic acid (Aldrich, Switzerland) was used as received.

Example 1

Preparation of Oligomers According to the Invention

Oligomeric Composition No 1:

In a round bottom flask of 50 ml, urea (2.66 g), 1,3,5-triazine-2,4,6-triamine (1.86 g), 2,2-dimethoxyacetaldehyde (60% w/w in water, 2.54 g), and oxalaldehyde (40% w/w in water, 8.58 g) were added in demineralised water (20.00 g). The pH, at 5.80-6.00, was adjusted with sodium hydroxide (30% w/w in water, 0.36 g) to pH=9-10. The mixture was heated at 60° C. for 20 minutes to give a solution (pH=6.70-7.00). Then nitric acid was added (30% w/w in water, 2.00 g) to fix pH at 4.50-4.70.

| Compound | Amount (g) | n (mol) | eq. | Ratio M/U | Ratio GY/DME | Ratio $NH_{2tot}/CHO_{tot}$ |
|---|---|---|---|---|---|---|
| Melamine | 1.86 | 14.7 | 1 | 1/3 | | 1/1 |
| Urea | 2.66 | 44.3 | 3 | | | |
| DME | 2.54 | 14.7 | 1 | | 4/1 | |
| GY | 8.58 | 59.1 | 4 | | | |

Oligomeric Composition No 2:

In a round bottom flask of 50 ml, oxalaldehyde (40% w/w in water, 2.11 g), 2,2-dimethoxyacetaldehyde (60% w/w in water, 1.68 g), 2-oxoacetic acid (50% w/w in water, 0.72 g), and 1,3,5-triazine-2,4,6-triamine (1.11 g) were added into demineralised water (1.90 g). The pH was adjusted with sodium hydroxide (30% w/w in water, 1.04 g) from 2.47 to 9.56. The mixture was heated at 45° C. for 25 minutes to give a solution (pH=9.10). Then demineralised water (8.35 g) was added and resin was stirred for 5 min (pH=9.09).

| Compound | Amount (g) | n (mol) | Ratio GY/DME/AGY | Ratio $NH_{2tot}/CHO_{tot}$ |
|---|---|---|---|---|
| DME | 1.68 | 9.69 | 3/2/1 | 1/1.65 |
| GY | 2.11 | 14.55 | | |
| AGY | 0.72 | 4.85 | | |
| Melamine | 1.11 | 8.78 | | |

Oligomeric Composition No 3:

In a round bottom flask of 50 ml, urea (2.66 g), 1,3,5-triazine-2,4,6-triamine (1.86 g), 2,2-dimethoxyacetaldehyde (60% w/w in water, 2.54 g), and oxalaldehyde (40% w/w in water, 3.76 g) were added in demineralised water (20.00 g). The pH, at 5.50, was adjusted with sodium hydroxide (30% w/w in water, 0.10 g) to pH=9.20. The mixture was heated at 60° C. for 20 minutes to give a solution (pH=6.70-7.00). Then nitric acid was added (30% w/w in water, 2.00 g) to fix pH at 4.50.

| Compound | Amount (g) | n (mmol) | eq. | Ratio M/U | Ratio GY/DME | Ratio $NH_{2tot}/CHO_{tot}$ |
|---|---|---|---|---|---|---|
| Melamine | 1.86 | 14.7 | 1 | 1/3 | | 2/1 |
| Urea | 2.66 | 44.3 | 3 | | | |
| DME | 2.54 | 14.7 | 1 | | 1.77/1 | |
| GY | 3.76 | 25.9 | 1.77 | | | |

Oligomeric Composition No 4:

In a round bottom flask of 50 mL, oxalaldehyde (40% w/w in water, 0.87 g), 2,2-dimethoxyacetaldehyde (60% w/w in water, 1.38 g), 2-oxoacetic acid (50% w/w in water, 0.59 g) and gluteraldehyde (25% w/w in water, 2.37 g), and 1,3,5-triazine-2,4,6-triamine (0.91 g) were added into demineralised water (1.60 g). The pH was adjusted with sodium hydroxide (30% w/w in water, 0.89 g) from 2.21 to 9.45. The mixture was heated at 45° C. for 25 minutes to give a solution (pH=8.73). Then demineralised water (6.80 g) was added and resin was stirred for 5 min.

| Compound | Amount (g) | n (mmol) | Ratio $NH_{2tot}/CHO_{tot}$ |
|---|---|---|---|
| DME | 1.38 | 7.96 | 1/1.65 |
| GY | 0.87 | 6.00 | |
| Glutaraldehyde | 2.37 | 5.93 | |
| AGY | 0.59 | 3.99 | |
| Melamine | 0.91 | 7.22 | |

Oligomeric Composition No 5:

In a round bottom flask of 50 mL, oxalaldehyde (40% w/w in water, 1.90 g), 2,2-dimethoxyacetaldehyde (60% w/w in water, 1.68 g), 2-oxoacetic acid (50% w/w in water, 0.72 g) and gluteraldehyde (25% w/w in water, 0.58 g), and 1,3,5-triazine-2,4,6-triamine (1.11 g) were added into demineralised water (1.90 g). The pH was adjusted with sodium hydroxide (30% w/w in water, 0.87 g) from 2.21 to 9.45. The mixture was heated at 45° C. for 25 minutes to give a solution (pH=8.73). Then demineralised water (8.40 g) was added and resin was stirred for 5 min.

| Compound | Amount (g) | n (mmol) | Ratio $NH_{2tot}/CHO_{tot}$ |
|---|---|---|---|
| DME | 1.68 | 9.69 | 1/1.65 |
| GY | 1.90 | 13.10 | |
| Glutaraldehyde | 0.58 | 1.45 | |
| AGY | 0.72 | 4.86 | |
| Melamine | 1.11 | 8.80 | |

Example 2

Preparation of Microcapsules with Polyisocyanates

Perfume Oil Composition:

| Raw material | Amount (g) |
|---|---|
| Romascone® [1] | 4.0 |
| Verdox® [2] | 4.0 |
| Lorysia® [3] | 4.0 |
| Lilial® [4] | 4.0 |
| Hexyl Salicylate | 4.0 |

[1] methyl 2,2-dimethyl-6-methylene-1-cyclohexanecarboxylate; origin: Firmenich SA, Geneva, Switzerland
[2] 2-tert-butyl-1-cyclohexyl acetate; origin: International Flavors & Fragrances, USA
[3] 4-(1,1-dimethylethyl)-1-cyclohexyl acetate; origin: Firmenich SA, Geneva, Switzerland
[4] 3-(4-tert-butylphenyl)-2-methylpropanal; origin: Givaudan SA, Vernier, Switzerland A: Preparation of Microcapsules with Oligomeric Composition No 1

General protocol: Solution of oligomeric composition no 1 (38 g) was dissolved in a solution of Ambergum® 1221 (a "polyol") and guanazole (a $C_{1-4}$ diamino compound). A solution of perfume oil and polyisocyanate was added and emulsified with ultra-turrax at 24000 rpm for 2 min (pH=5.00-5.60). The reaction mixture was heated at 60° C. or 80° C. for 4 hours, then cooled down to room temperature (pH=5.00-5.50). The slurry of microcapsules was neutralized with a solution of sodium hydroxide (30 wt % in water).

Microcapsule 1:

Microcapsules Prepared in the Presence of Desmodur® N100 as Polyisocyanate and Ambergum® 1221 as Polyol

| Raw material | Amount (g) | % (w/w) |
|---|---|---|
| Oligomeric composition n°1 (26.8 wt % in water) | 38 | 6.8 |
| Polyol (Ambergum® 1221, 2 wt % in water) | 60 | 0.8 |
| Guanazole | 4 | 2.7 |
| Perfume oil | 40 | 26.6 |
| Desmodur® N100 (a polyisocyanate) | 7.45 | 5.0 |
| Water | to balance | 58.1 |
| Total | 150.17 | 100 |

Microcapsule 2:

Microcapsules Prepared in the Presence of Desmodur® N100 as Polyisocyanate and Blanose™ 12M8P as Polyol

| Raw material | Amount (g) | % (w/w) |
|---|---|---|
| Oligomeric composition n°1 (26.9 wt % in water) | 28.5 | 6.8 |
| Polyol (Blanose™ 12M8P, 2 wt % in water) | 45 | 0.8 |
| Guanazole | 3 | 2.7 |
| Perfume oil | 30 | 26.6 |
| Desmodur® N100 (a polyisocyanate) | 5.6 | 5.0 |
| Water | to balance | 58.1 |
| Total | 112.7 | 100 |

Microcapsule 3:

Microcapsules Prepared in the Presence of Hexamethylene Diisocyanate

| Raw material | Amount (g) | % (w/w) |
|---|---|---|
| Oligomeric composition n°1 (26.9 wt % in water) | 28.5 | 6.9 |
| Polyol (Ambergum® 1221, 2 wt % in water) | 45 | 0.8 |
| Guanazole | 3 | 2.7 |
| Perfume oil | 30 | 27.1 |
| Hexamethylene diisocyanate | 3.93 | 3.5 |
| Water | to balance | 59.0 |
| Total | 110.74 | 100 |

Microcapsule 4:

Microcapsules Prepared in the Presence of Takenate® D-110N

| Raw material | Amount (g) | % (w/w) |
|---|---|---|
| Oligomeric composition n°1 (26.9 wt % in water) | 28.5 | 6.5 |
| Polyol (Ambergum 1221, 2 wt % in water) | 45 | 0.8 |
| Guanazole | 3 | 2.5 |
| Perfume oil | 30 | 25.4 |
| Takenate® D-110N (a polyisocyanate) | 10.9 | 9.2 |
| Water | to balance | 55.6 |
| Total | 118.1 | 100 |

Microcapsule 5:

Microcapsules Prepared in the Presence of Isophorone Diisocyanate

| Raw material | Amount (g) | % (w/w) |
|---|---|---|
| Oligomeric composition n°1 (26.9 wt % in water) | 28.5 | 6.6 |
| Polyol (Ambergum® 1221, 2 wt % in water) | 45 | 0.8 |
| Guanazole | 3 | 2.5 |
| Perfume oil | 30 | 25.8 |
| Isophorone diisocyanate | 9 | 7.7 |
| Water | to balance | 56.6 |
| Total | 116.2 | 100 |

B: Preparation of Microcapsules with Oligomeric Composition No 2

General protocol: A solution of oligomeric composition no 2 (16.9 g) was introduced into a 200 mL reactor in the presence of guanazole (a $C_{1-4}$ diamino compound, 0.98 g) and demineralised water (32.5 g, pH=9.00-9.50). A solution of perfume oil and polyisocyanate (21.00 g) was added and emulsified with Ultra-turrax at 21500-24000 rpm for 2 min (pH=8.50-9.00). The pH was adjusted to 5.00-5.50 with formic acid (30% w/w in water). Reaction mixture was heated at 60° C. for 4 h, cooled down to room temperature (pH=5.50-6.00). The slurry of microcapsules was neutralized with a solution of sodium hydroxide (30 wt % in water).

Microcapsule 6:

Microcapsules Prepared in the Presence of Desmodur® N100

| Raw material | Amount (g) | % (w/w) |
|---|---|---|
| Oligomeric composition n°2 (19.6 wt % in water) | 16.9 | 4.5 |
| Guanazole | 0.98 | 1.3 |
| Perfume oil | 21.0 | 28.6 |
| Desmodur ® N100 (a polyisocyanate) | 1.81 | 2.5 |
| Formic acid (30 wt % in water) | 0.14 | 0.06 |
| Water | to balance | 63.04 |
| Total | 73.44 | 100 |

Microcapsule 7:

Microcapsules Prepared in the Presence of Isophorone Diisocyanate

| Raw material | Amount (g) | % (w/w) |
|---|---|---|
| Oligomeric composition n°2 (19.6 wt % in water) | 16.9 | 4.5 |
| Guanazole | 0.98 | 1.3 |
| Perfume oil | 21.0 | 28.4 |
| Isophorone diisocyanate | 2.17 | 2.9 |
| Formic acid (30 wt % in water) | 0.18 | 0.07 |
| Water | to balance | 62.83 |
| Total | 73.86 | 100 |

Microcapsule 8:

Microcapsules Prepared in the Presence of Hexamethylene Diisocyanate

| Raw material | Amount (g) | % (w/w) |
|---|---|---|
| Oligomeric composition n°2 (19.6 wt % in water) | 17.0 | 4.5 |
| Guanazole | 0.98 | 1.3 |
| Perfume oil | 21.0 | 28.6 |
| Hexamethylene diisocyanate | 1.64 | 2.2 |
| Formic acid (30 wt % in water) | 0.19 | 0.08 |
| Water | to balance | 63.32 |
| Total | 73.46 | 100 |

Microcapsule 9:

Microcapsules Prepared in the Presence of Takenate® D-110N

| Raw material | Amount (g) | % (w/w) |
|---|---|---|
| Oligomeric composition n°2 (19.6 wt % in water) | 16.9 | 4.5 |
| Guanazole | 0.98 | 1.3 |
| Perfume oil | 21.0 | 28.3 |
| Takenate ® D-110N (a polyisocyanate) | 2.64 | 3.6 |
| Formic acid (30 wt % in water) | 0.16 | 0.06 |
| Water | to balance | 62.24 |
| Total | 74.33 | 100 |

Microcapsule 10:

Microcapsules Prepared in the Presence of Takenate® D-110N as Polyisocyanate and Ambergum® 1221 as Polyol

| Raw material | Amount (g) | % (w/w) |
|---|---|---|
| Oligomeric composition n°2 (19.6 wt % in water) | 33.97 | 4.4 |
| Guanazole | 1.96 | 1.3 |
| Perfume oil | 42.0 | 28.0 |
| Takenate ® D-110N (a polyisocyanate) | 5.28 | 3.5 |
| Formic acid (30 wt % in water) | 0.42 | 0.08 |
| Polyol (Ambergum ® 1221, 2 wt % in water) | 66.38 | 0.89 |
| Water | to balance | 61.83 |
| Total | 150.01 | 100 |

Microcapsule 11:

Microcapsules Prepared in the Presence of Takenate® D-110N as Polyisocyanate, Ambergum® 1221 as Polyol, and Guanidine Carbonate as a Diamino Compound

| Raw material | Amount (g) | % (w/w) |
|---|---|---|
| Oligomeric composition n°2 (19.6 wt % in water) | 16.63 | 4.37 |
| Guanidine carbonate | 0.89 | 1.19 |
| Perfume oil | 21.00 | 28.1 |
| Takenate ® D-110N (a polyisocyanate) | 2.64 | 3.54 |
| Formic acid (30 wt % in water) | 0.21 | 0.08 |
| Polyol (Ambergum ® 1221, 2 wt % in water) | 33.19 | 0.89 |
| Water | to balance | 61.83 |
| Total | 74.56 | 100 |

C: Preparation of Microcapsules with Oligomeric Composition No 3

General protocol: Solution of oligomeric composition no 3 (32.9 g) was dissolved in a solution of Ambergum® 1221 (a "polyol") and guanazole (a $C_{1-4}$ diamino compound). A solution of perfume oil and polyisocyanate was added and emulsified with ultra-turrax at 24000 rpm for 2 min (pH=5.00-5.60). The reaction mixture was heated at 60° C. for 4 hours, then cooled down to room temperature (pH=5.00-5.50).

Microcapsule 12:

Microcapsules Prepared in the Presence of Takenate® D-110N as Polyisocyanate and Ambergum® 1221 as Polyol

| Raw material | Amount (g) | % (w/w) |
|---|---|---|
| Oligomeric composition n°3 (24.8 wt % in water) | 32.9 | 5.4 |
| Polyol (Ambergum ® 1221, 2 wt % in water) | 60 | 0.8 |
| Guanazole | 4 | 2.6 |
| Perfume oil | 40 | 26.4 |
| Takenate ® D-110N (a polyisocyanate) | 14.54 | 9.6 |
| Water | to balance | 55.2 |
| Total | 151.44 | 100 |

D: Preparation of Microcapsules 13 with Oligomeric Composition n° 4

General protocol: Solution of oligomeric composition no 4 (15.41 g) was dissolved in a solution of Ambergum® 1221 (a "polyol") and guanazole (a $C_{1-4}$ diamino compound). A solution of perfume oil and polyisocyanate was added and emulsified with ultra-turrax at 24000 rpm for 2 min (pH=5.22). Reaction mixture was heated at 45° C. for 1 h, at 60° C. for 1 h, at 80° C. for 3 h and finally cooled down to room temperature (pH=5.00-5.50).

Microcapsule 13:

Microcapsules Prepared in the Presence of Takenate® D-110N as Polyisocyanate and Ambergum® 1221 as Polyol

| Raw material | Amount (g) | % (w/w) |
|---|---|---|
| Oligomeric composition n°4 (21.0 wt % in water) | 15.41 | 4.62 |
| Polyol (Ambergum ® 1221, 2 wt % in water) | 27.22 | 0.78 |
| Guanazole | 0.80 | 1.14 |
| Perfume oil | 25.83 | 36.87 |
| Takenate ® D-110N (a polyisocyanate) | 2.17 | 3.10 |
| Water | To balance | 53.49 |
| Total | 70.06 | 100 |

E: Preparation of Microcapsules 14 with Oligomeric Composition n° 5

General protocol: Solution of oligomeric composition no 5 (xxx g) was dissolved in a solution of Ambergum® 1221 (a "polyol") and guanazole (a $C_{1-4}$ diamino compound). A solution of perfume oil and polyisocyanate was added and emulsified with ultra-turrax at xxx rpm for xxx min (pH=5.00-5.60). Reaction mixture was heated at 45° C. for 1 h, at 60° C. for 1 h, at 80° C. for 3 h and finally cooled down to room temperature (pH=5.00-5.50).

Microcapsule 14:

Microcapsules Prepared in the Presence of Takenate® D-110N as Polyisocyanate and Ambergum® 1221 as Polyol

| Raw material | Amount (g) | % (w/w) |
|---|---|---|
| Oligomeric composition n°5 (21.2 wt % in water) | 17.16 | 4.84 |
| Polyol (Ambergum ® 1221, 2 wt % in water) | 33.19 | 0.88 |
| Guanazole | 0.98 | 1.30 |
| Perfume oil | 21.00 | 27.93 |
| Takenate ® D-110N (a polyisocyanate) | 2.64 | 3.51 |
| Water | To balance | 61.54 |
| Total | 75.18 | 100 |

Example 3

Preparation of Microcapsules with Polyoxiran

A: Preparation of Microcapsules with Oligomeric Composition No 1

General protocol: Solution of oligomeric composition no 1 (38 g) was dissolved in a solution of Ambergum® 1221 (a "polyol") and guanazole (a "$C_{1-4}$ diamino compound"). A solution of perfume oil and polyoxiran was added and emulsified with ultra-turrax at 24000 rpm for 2 min (pH=5.00-5.60). The reaction mixture was heated at 60° C. or 80° C. for 4 hours, then cooled down to room temperature (pH=5.00-5.50). The slurry of microcapsules was neutralized with a solution of sodium hydroxide (30 wt % in water).

Microcapsule 15:

Microcapsules Prepared in the Presence of Ethyleneglycol Diglycidylether (a Polyoxiran)

| Raw material | Amount (g) | % (w/w) |
|---|---|---|
| Oligomeric composition n°1 (26.9 wt % in water) | 28.5 | 6.7 |
| Polyol (Ambergum ® 1221, 2 wt % in water) | 45 | 0.8 |
| Guanazole | 3 | 2.6 |
| Perfume oil | 30 | 26.4 |
| Ethyleneglycol diglycidylether (a polyoxiran) | 7 | 6.2 |
| Water | to balance | 57.3 |
| Total | 113.6 | 100 |

Microcapsule 16:

The Reaction Mixture was Heated at 80° C. For 4 Hours

| Raw material | Amount (g) | % (w/w) |
|---|---|---|
| Oligomeric composition n°1 (26.9 wt % in water) | 28.5 | 6.7 |
| Polyol (Ambergum ® 1221, 2 wt % in water) | 45 | 0.8 |
| Guanazole | 3.0 | 2.6 |
| Perfume oil | 30.0 | 26.4 |
| Ethyleneglycol diglycidylether (a polyoxiran) | 7.0 | 6.2 |
| Water | to balance | 57.3 |
| Total | 113.6 | 100 |

Microcapsule 17:

Microcapsules Prepared in the Presence of Resorcinol Diglycidylether

| Raw material | Amount (g) | % (w/w) |
|---|---|---|
| Oligomeric composition n°1 (26.9 wt % in water) | 28.5 | 6.6 |
| Polyol (Ambergum ® 1221, 2 wt % in water) | 45 | 0.8 |
| Guanazole | 3.0 | 2.6 |
| Perfume oil | 30 | 25.9 |
| Resorcinol diglycidylether (a polyoxiran) | 9.0 | 7.8 |
| Water | to balance | 56.3 |
| Total | 115.9 | 100 |

Microcapsule 18:

Microcapsules Prepared in the Presence of Resorcinol Diglycidylether at 80° C. For 4 h

| Raw material | Amount (g) | % (w/w) |
|---|---|---|
| Oligomeric composition n°1 (26.9 wt % in water) | 28.5 | 6.6 |
| Polyol (Ambergum ® 1221, 2 wt % in water) | 45 | 0.8 |
| Guanazole | 3.0 | 2.6 |
| Perfume oil | 30 | 25.9 |
| Resorcinol diglycidylether (a polyoxiran) | 9.0 | 7.8 |
| Water | to balance | 56.3 |
| Total | 115.8 | 100 |

Microcapsule 19:

Microcapsules Prepared in the Presence of Trimethylolpropane Triglycidylether

| Oligomeric composition n°1 (26.9 wt % in water) | 28.5 | 6.7 |
|---|---|---|
| Polyol (Ambergum ® 1221, 2 wt % in water) | 45 | 0.8 |
| Guanazole | 3 | 2.6 |
| Perfume oil | 30 | 26.1 |
| Trimethylolpropane triglycidylether (a polyoxiran) | 8.1 | 7.0 |
| Water | to balance | 56.8 |
| Total | 115.1 | 100 |

Microcapsule 20:

Microcapsules Prepared in the Presence of Trimethylolpropane Triglycidylether at 80° C. For 4 h

| Raw material | Amount (g) | % (w/w) |
|---|---|---|
| Oligomeric composition n°1 (26.9 wt % in water) | 28.5 | 6.7 |
| Polyol (Ambergum ® 1221, 2 wt % in water) | 45 | 0.8 |
| Guanazole | 3 | 2.6 |

-continued

| Raw material | Amount (g) | % (w/w) |
|---|---|---|
| Perfume oil | 30 | 26.1 |
| Trimethylolpropane triglycidylether (a polyoxiran) | 8.1 | 7.0 |
| Water | to balance | 56.8 |
| Total | 115.0 | 100 |

B: Preparation of Microcapsules with Oligomeric Composition No 2

Microcapsule 21:

Oligomeric composition no 2 (16.9 g) was introduced into a 200 mL reactor in the presence of guanazole (a "$C_{1-4}$ diamino compound", 0.98 g) and demineralised water (32.5 g, pH=8.33). A solution of perfume oil (21.00 g) and trimethylolpropane triglycidylether (1.97 g) was added and emulsified with Ultra-turrax at 24000 rpm for 2 min (pH=7.75). The pH was adjusted with formic acid (30% w/w in water, 0.16 g, pH=5.34). Reaction mixture was heated at 80° C. for 4 h, and finally cooled down to r.t. (pH=5.67). The slurry of microcapsules was neutralized with a solution of sodium hydroxide (30 wt % in water).

| Raw material | Amount (g) | % (w/w) |
|---|---|---|
| Oligomeric composition n°2 (19.6 wt % in water) | 16.9 | 4.5 |
| Guanazole | 0.98 | 1.3 |
| Perfume oil | 21.0 | 28.5 |
| Trimethylolpropane triglycidylether (a polyoxiran) | 1.97 | 2.7 |
| Formic acid (30 wt % in water) | 0.14 | 0.06 |
| Water | to balance | 62.94 |
| Total | 73.61 | 100 |

Example 4

Microcapsules According to the Prior Art (Comparison)

A: Microcapsules Obtained Using Prior Art PCT/IB2011/052700 Oligomeric Composition and Invention's Process Comparative Microcapsule 1:

Preparation with Oligomeric Composition No 1

| Raw material | Amount (g) | % (w/w) |
|---|---|---|
| Oligomeric composition n°1 (26.9 wt % in water) | 38 | 7.1 |
| Polyol (Ambergum ® 1221, 2 wt % in water) | 60 | 0.8 |
| Guanazole | 4 | 2.8 |
| Perfume oil | 40 | 28 |
| Water | to balance | 61.3 |
| Total | 142.68 | 100 |

Comparative Microcapsule 2:

Preparation with Oligomeric Composition No 1 and Blanose™ 12M8P (a "Polyol", 2% w/w in Water, 45.00 g), Used Instead of Ambergum® 1221

| Raw material | Amount (g) | % (w/w) |
|---|---|---|
| Oligomeric composition n°1 (26.9 wt % in water) | 28.5 | 7.2 |
| Polyol (Blanose ™ 12M8P, 2 wt % in water) | 45 | 0.8 |
| Guanazole | 3 | 2.8 |
| Perfume oil | 30 | 28.0 |
| Water | to balance | 61.2 |
| Total | 107.1 | 100 |

Comparative Microcapsule 3:

Preparation with Oligomeric Composition No 2

| Raw material | Amount (g) | % (w/w) |
|---|---|---|
| Oligomeric composition n°2 (19.6 wt % in water) | 16.9 | 4.6 |
| Guanazole | 0.98 | 1.4 |
| Perfume oil | 21.0 | 29.3 |
| Formic acid (30 wt % in water) | 0.24 | 0.1 |
| Water | to balance | 64.6 |
| Total | 71.73 | 100 |

B: Microcapsules Obtained Using Prior Art WO 2009/100553 Oligomeric Composition and Invention's Process Oligomeric Composition: According to Prior Art WO 2009/100553

In a round bottom flask of 250 ml, melamine (11.2 g, 89 mmol) and DME (30.8 g, 178 mmol) were dissolved in water (3.7 g, 205 mmol). The pH was adjusted with 0.27 g of sodium hydroxide (pH=9.53). The mixture was heated at 60° C. for 2 h to give a solution. Then, formic acid (1.02 g, 22 mmol) was added to fix pH at 4.50. The mixture was heated at 60° C. for 4 h. Solution was stored in the fridge (pH=4.23). MW=350 g/mol (measured by SEC).

TABLE

Ratio of the various starting materials

| Compound | Amount (g) | n (mol) | eq. | Ratio $NH_{2tot}/CHO_{tot}$ |
|---|---|---|---|---|
| Melamine | 11.2 | 89 | 1 | 3/2 |
| DME | 30.8 | 178 | 2 | |

Comparative Capsules 4:

In a 200 mL reactor, colloidal stabilizer (Gantrez AN-119BF, 0.81 g) and polyol (2 g, Resorcinol, 30% in water) were dissolved in water (25.00 g) and added into oligomeric composition (5.51 g). Perfume oil (20.00 g) was added and the reaction mixture was sheared with ultra turrax at 21000 rpm for 2 minutes. Reaction mixture was then stirred at 300 r.p.m. and heated at 45° C. for 1 h then at 60° C. for 1 h, and finally at 75° C. for 3 h. The resulting slurry was cooled down (pH=5.39) and neutralized with a solution of sodium hydroxide (30% in water, 0.35 g, pH=6.70).

| Raw material | Amount (g) | % (w/w) |
|---|---|---|
| Colloidal stabilizer (Gantrez ® AN-119BF) | 0.81 | 1.5 |
| Polyol (Resorcinol, 30% in water) | 2.00 | 1.1 |
| Demineralised water | to balance | 56.4 |
| Oligomeric composition (~53.9% in water) | 5.51 | 4.2 |
| Perfume oil | 20.00 | 36.8 |
| Total | 53.67 | 100 |

Example 5

Aqueous solutions of cationic copolymers were added to anionic capsules at the end of the synthesis. Copolymers are listed below.

| Code | Copolymers | Supplier | Solution in water (wt %) | Mw (g/mol) | Cationic activity (meq/g) |
|---|---|---|---|---|---|
| A | Salcare SC 60 | BASF | 3 | 1'000'000 | 1.9 |
| B | Luviquat PQ 11 | BASF | 20 | 1'000'000 | 0.8 |
| C | Luviquat Excellence | BASF | 40 | 40'000 | 6.1 |
| D | Luviquat FC 550 | BASF | 40 | 80'000 | 3.3 |
| E | Luviquat FC 370 | BASF | 40 | 100'000 | 2.0 |
| F | Luviquat Style | BASF | 20 | 400'000 | 3.0 |
| G | Sensomer CI 50 | Lubrizol | 32 | 2'000'000 | unknown |
| H | Sensomer CT 400 | Lubrizol | 1.2 | unknown | 3.0 |
| I | Sensomer CT 250 | Lubrizol | 1.2 | unknown | 1.9 |
| J | Jaguar C17 | Rhodia | 1 | unknown | unknown |
| K | Jaguar C162 | Rhodia | 1 | unknown | unknown |
| L | Jaguar Excel | Rhodia | 1 | unknown | unknown |
| M | Jaguar C14 S | Rhodia | 1 | unknown | unknown |

Different amounts of copolymer solutions were added to 5 g of microcapsules dispersions and the zeta potential of the dispersions was measured. The lowest concentration of each copolymer giving a positive difference of potential was recorded below.

In the presence of microcapsules 10:

| Copolymer | Amount of copolymer solution (g) | Concentration (wt %) | Zeta potential (mV) |
|---|---|---|---|
| None | | | −37 |
| Salcare SC 60 | 4.660 | 1.45 | +26 |
| Luviquat PQ 11 | 0.700 | 2.46 | −1 |
| Luviquat Excellence | 0.175 | 1.35 | +31 |
| Luviquat FC 550 | 0.175 | 1.35 | +20 |
| Luviquat FC 370 | 0.350 | 2.62 | +21 |
| Luviquat Style | 0.700 | 2.46 | +44 |
| Sensomer CI 50 | 0.872 | 4.75 | +14 |
| Sensomer CT 400 | 11.660 | 0.84 | +38 |
| Sensomer CT 250 | 11.660 | 0.84 | +31 |
| Jaguar C17 | 20.970 | 0.81 | +11 |
| Jaguar C162 | 34.950 | 0.87 | +7 |
| Jaguar Excel | 27.960 | 0.85 | +7 |
| Jaguar C14 S | 27.960 | 0.85 | +3 |

In the presence of microcapsule 12:

| Copolymer | Amount of copolymer solution (g) | Concentration (wt %) | Zeta potential (mV) |
|---|---|---|---|
| None | | | −49 |
| Salcare SC 60 | 2.330 | 0.95 | +17 |
| Luviquat PQ 11 | 0.700 | 2.46 | +16 |
| Luviquat Excellence | 0.175 | 1.35 | +48 |
| Luviquat FC 550 | 0.175 | 1.35 | +36 |
| Luviquat FC 370 | 0.175 | 1.35 | +26 |
| Luviquat Style | 0.350 | 1.31 | +37 |
| Sensomer CI 50 | 0.654 | 3.70 | +18 |
| Sensomer CT 400 | 5.83 | 0.65 | +19 |
| Sensomer CT 250 | 5.83 | 0.65 | +16 |
| Jaguar C17 | 13.98 | 0.74 | +7 |
| Jaguar C162 | 20.97 | 0.81 | +2 |
| Jaguar Excel | 20.97 | 0.81 | +6 |
| Jaguar C14 S | 20.97 | 0.81 | +4 |

Example 6

Use in Application of the Invention's Microcapsules

Body Wash Application

TABLE

| Body wash formulation | |
|---|---|
| Ingredients | % w/w |
| 1. Water deionised | 58.40 |
| 2. Carbopol ® Aqua CC Polymer Polyacrylate-1 Crosspolymer (Noveon) | 8.00 |
| 3. Citric Acid (40% aqueous solution) | 0.50 |
| 4. Zetesol AO 328 U Sodium C12-C15 Pareth Sulfate (Zschimmer & Schwarz) | 25.00 |
| 5. Tego ® Betain F 50 Cocamidopropyl Betaine (Goldschmidt AG) | 4.00 |
| 6. Glydant ™ Plus Liquid DMDM Hydantoin and Iodopropynyl Butylcarbamate (Lonza) | 0.10 |
| 7. Sodium Chloride (20% aqueous solution) | 4.00 |

Capsules were introduced in Body Wash formulation to obtain a concentration of perfume at 0.2% w/w. Dispersions were stored at room temperature for 24 hours. The body wash formulation (1 mL) was diluted in water (4 mL) and then extracted with isooctane containing 1,4-dibromobenzene as internal standard (5 mL). Organic solutions are then analyzed by GC to measure the leakage of perfume. The results on oil-leakage of the microcapsules (%) are obtained from equation 1:

$$\text{Oil leakage (\%)} = 100 \times \frac{\text{mass of oil detected in aqueous phase}}{\text{mass of oil introduced in dispersion}} \quad (1)$$

The corresponding values are reported in the following table with a mean error of 5%:

| Example | Microcapsules | $t_0$ | 25° C. | | | | | 40° C. | | | | |
|---|---|---|---|---|---|---|---|---|---|---|---|---|
| | | | 1 w | 2 w | 4 w | 8 w | 12 w | 1 w | 2 w | 4 w | 8 w | 12 w |
| 2A | 1 | 2 | 2 | 0.5 | 1 | 2 | 1 | 2 | 0.4 | 2 | 1 | 1 |
| | 2 | 2 | 0 | 2 | 2 | 1 | 2 | 0 | 1 | 2 | 1 | 2 |
| | 3 | 1 | 2 | 3 | 3 | 5 | 7 | 9 | 9 | 7 | 11 | 13 |
| | 4 | 2 | 1 | 2 | 1 | 1 | 2 | 1 | 1 | 1 | 1 | 2 |
| | 5 | 2 | 3 | 3 | 6 | 7 | | 20 | 17 | 17 | 24 | |
| 2B | 6 | 2 | 2 | 2 | 2 | 1 | 1 | 2 | 2 | 3 | 2 | 1 |
| | 7 | 2 | 16 | 16 | 24 | — | — | 54 | 62 | — | — | — |
| | 8 | 2 | 5 | 7 | 7 | 10 | 10 | 15 | 25 | 24 | 30 | — |
| | 9 | 1 | 1 | 1 | 2 | 2 | 1 | 1 | 2 | 2 | 2 | 1 |
| | 10 | 0 | 0 | | | | | | | | | |
| | 11 | 0 | 0 | — | — | — | — | | | | | |
| 2E | 14 | 0 | 0 | — | — | — | — | | | | | |
| 3A | 18 | 2 | 27 | 31 | — | — | — | 34 | 40 | — | — | — |
| 4 | Comparative microcapsule 1 | 4 | 90 | — | — | — | — | 100 | — | — | — | — |
| | Comparative microcapsule 2 | 2 | 75 | — | — | — | — | 44 | — | — | — | — |
| | Comparative microcapsule 3 | 2 | 76 | — | — | — | — | 95 | — | — | — | — |
| | Comparative microcapsule 4 | 42 | — | — | — | — | — | 100 | — | — | — | — | w = week/— = Measurement stopped

As can be seen, all invention's microcapsules are more stable toward oil-leakage upon storage when compared to prior art microcapsules which are $CH_2O$-free.

Softener Application

Microcapsules were diluted in a fabric softener (composition: Stepantex® VK90 (Stepan) 16.5%, calcium chloride 0.2%, water 83.3%) to obtain a concentration of perfume at 0.8% w/w. Dispersions were stored at room temperature for 24 hours. An aliquot of softener (1 ml) was diluted in water (4 ml) and then extracted with isooctane (5 mL) containing 1,4-dibromobenzene as internal standard (150 mg/L). Organic solutions were then analyzed by GC to measure the leakage of perfume. The results on oil-leakage of the microcapsules (%) are obtained from equation 1. The corresponding values are reported in the following table:

| Microcapsules | $t_0$ | 25° C. | | | | | 43° C. | | | | |
|---|---|---|---|---|---|---|---|---|---|---|---|
| | | 1 w | 2 w | 4 w | 8 w | 12 w | 1 w | 2 w | 4 w | 8 w | 12 w |
| 1 | 0 | 2 | 0 | 0 | 1 | 0 | 1 | 1 | 0 | 2 | 3 |
| 6 | 0 | 0 | 0 | 0 | 0 | 0 | 3 | 3 | 4 | 5 | 9 |
| 10 | 0 | 0 | — | — | — | — | 0 | — | — | — | — |
| 11 | 0 | 0 | — | — | — | — | 0 | — | — | — | — |
| 14 | 0 | 0 | — | — | — | — | 0 | — | — | — | — |
| Comparative microcapsule 1 | 4 | 100 | — | — | — | — | 100 | — | — | — | — |
| Comparative microcapsule 2 | 4 | 100 | — | — | — | — | 100 | — | — | — | — |
| Comparative microcapsule 3 | 2 | 100 | — | — | — | — | 100 | — | — | — | — |
| Comparative microcapsule 4 | 94 | 100 | — | — | — | — | 100 | — | — | — | — | w = week/— = Measurement stopped

As can be seen from Table 3B all invention's microcapsules are more stable toward oil-leakage upon storage when compared to prior art microcapsules which are $CH_2O$-free.

What is claimed is:

1. A process for the preparation of a core-shell microcapsule, said process comprising the steps of:
   1) preparing an oligomeric composition comprising the reaction product of, or obtainable by reacting together:
      a) a polyamine component in the form of melamine or of a mixture of melamine and at least one $C_{1-4}$ compound comprising two $NH_2$ functional groups;
      b) an aldehyde component in the form of a mixture of glyoxal, a $C_{4-6}$ 2,2-dialkoxy-ethanal and optionally a glyoxalate, said mixture having a molar ratio glyoxal/$C_{4-6}$ 2,2-dialkoxy-ethanal comprised between 1/1 and 10/1; and
      c) a protic acid catalyst;
   2) preparing an oil-in-water dispersion, wherein the droplet size is comprised between 1 and 600 μm, and comprising:
      i) an oil;
      ii) a water medium;
      iii) at least an oligomeric composition as obtained in step 1);
      iv) at least a cross-linker selected amongst:
         A) $C_4$-$C_{12}$ aromatic or aliphatic di- or tri-isocyanates and their biurets, triurets, trimers and trimethylol propane-adduct; and/or
         B) a di- or tri-oxiran compounds of formula A-(oxiran-2-ylmethyl)$_n$ wherein n stands for 2 or 3 and A represents a $C_2$-$C_6$ group optionally comprising from 2 to 6 nitrogen and/or oxygen atoms;
    v) optionally a $C_{1-4}$ compound comprising two $NH_2$ functional groups;
3) heating said dispersion;
4) cooling said dispersion; and
5) optionally adding to the dispersion of step 4) at least one cationic polymer and/or urea or ethylene urea; and
6) optionally drying the final dispersion to obtain the dried core-shell microcapsule.

2. A process according to claim 1, wherein the dispersion comprises:
between 10% and 50% of oil;
between 1% and 20% of oligomeric composition;
between 0.5% and 15% of at least a cross-linker percentage being expressed on a w/w basis relative to the total weight of the dispersion.

3. A process according to claim 1, wherein the water medium comprises between 0% and 5% of at least a stabilizer and between 0% and 10% of at least a polyol, percentage being expressed on a w/w basis relative to the total weight of the dispersion.

4. A process according to claim 3, wherein said stabilizer is an ionic surfactant and said polyol is an aliphatic polymeric polyol.

5. A process according to claim 1, wherein said polyamine component is a mixture of melamine and at least one compound selected amongst urea, 1H-1,2,4-triazole-3,5-diamine and mixtures thereof, and the molar ratio melamine/$C_{1-4}$ compound comprising two $NH_2$ functional groups comprised between 2/1 and 1/3.

6. A process according to claim 1, wherein said aldehyde component is a mixture of glyoxal and at least one of a glyoxalate, 2,2-dimethoxy-ethanal, 2,2-diethoxy-ethanal and mixtures thereof, and has a molar ratio glyoxal/2,2-dialkoxy-ethanal comprised between 2.2/1 and 6.5/1 and the molar ratio glyoxal/glyoxalate is comprised between 4/1 and 1/1.

7. A process according to claim 1, wherein there is added an amount of at least one cationic polymer comprised between 0% and 60% percentage being expressed on a w/w basis relative to the total weight of the resin.

8. A process according to claim 1, wherein said di- or thi-isocyanate is selected amongst hexamethylene diisocyanate, isophorone diisocyanate, xylylene diisocyanate, toluene diisocyanate, a trimethylol propane-adduct of toluene diisocyanate, a trimethylol propane-adduct of xylylene diisocyanate, a trimer of hexamethylene diisocyanate, a trimer of isophorone diisocyanate, a trimethylol propane-adduct of hexamethylene diisocyanate or a biuret of hexamethylene diisocyanate.

9. A process according to claim 1, wherein said di- or tri-oxiran compound is selected amongst 1,3,5-tris(oxiran-2-ylmethyl)-1,3,5-triazinane-2,4,6-trione, 4-(oxiran-2-ylmethoxy)-N,N-bis(oxiran-2-ylmethyl)aniline, 1,3-bis(oxiran-2-ylmethoxy)benzene, 1,2-bis(oxiran-2-ylmethoxy)ethane and 2,2'-(2-ethyl-2-((oxiran-2-ylmethoxy)methyl)propane-1,3-diyl)bis(oxy)bis(methylene)dioxirane.

\* \* \* \* \*